United States Patent [19]

Swedlow et al.

[11] Patent Number: 5,746,697
[45] Date of Patent: May 5, 1998

[54] MEDICAL DIAGNOSTIC APPARATUS WITH SLEEP MODE

[75] Inventors: David B. Swedlow, Danville; Michael J. Bernstein, San Ramon; Charles E. Porges, Orinda; James E. Luecke, Dublin; Michael W. Nootbaar, Benicia, all of Calif.

[73] Assignee: Nellcor Puritan Bennett Incorporated, Pleasanton, Calif.

[21] Appl. No.: 599,255

[22] Filed: Feb. 9, 1996

[51] Int. Cl.$^6$ .................................................. A61B 5/00
[52] U.S. Cl. .................................................. 600/323
[58] Field of Search ........................ 128/633, 630, 128/632, 670; 607/16; 356/41

[56] References Cited

U.S. PATENT DOCUMENTS

| | | | |
|---|---|---|---|
| 4,404,972 | 9/1983 | Gordon et al. | 607/16 |
| 4,554,920 | 11/1985 | Baker, Jr. et al. | 128/419 |
| 4,561,442 | 12/1985 | Vollmann et al. | 128/419 |
| 4,716,463 | 12/1987 | Stacy et al. | 358/190 |
| 4,750,495 | 6/1988 | Moore et al. | 128/419 |
| 4,765,340 | 8/1988 | Sakai et al. | 128/633 |
| 4,856,524 | 8/1989 | Baker, Jr. | 128/419 |
| 4,924,496 | 5/1990 | Figa et al. | 379/142 |
| 5,142,684 | 8/1992 | Perry et al. | 395/750 |
| 5,201,059 | 4/1993 | Nguyen | 395/800 |
| 5,342,406 | 8/1994 | Thompson | 607/22 |
| 5,368,026 | 11/1994 | Swedlow et al. | 128/633 |

FOREIGN PATENT DOCUMENTS

WO 95/10222  4/1995  WIPO.

OTHER PUBLICATIONS

"Hands-on investigations help exploit CMOS designs", Robert H. Cushman, 2119 E.D.N. Electrical Design News, vol. 28, No. 8, Apr. '83, Boston, Mass., USA.

"Sampling Intervals for Clinical Monitoring of Variables During Anesthesia", Joachim S. Gravenstein, MD, et al., Journal of Clinical Monitoring, vol. 5, No. 1, Jan. 1989, pp. 17–21.

Primary Examiner—Jennifer Bahr
Assistant Examiner—Eric F. Winakur
Attorney, Agent, or Firm—Townsend and Townsend & Crew LLP

[57] ABSTRACT

A method and apparatus for conserving power in a medical diagnostic apparatus by using a sleep mode during a monitoring state. The invention monitors physiological parameters of the patient and enters a sleep mode only after they have been stable for a predetermined period of time. The apparatus is periodically awakened from the sleep mode to take additional measurements and to ascertain that the stability of the physiological parameters has not changed.

29 Claims, 3 Drawing Sheets

MEDICAL DIAGNOSTIC APPARATUS WITH SLEEP MODE

BACKGROUND OF THE INVENTION

The present invention relates to medical diagnostic devices, and particularly to battery-powered pulse oximeters.

Diagnostic monitors are used to monitor various physiological parameters of a patient. In particular, such monitors are used for heart rate, respiration rate, blood pressure, temperature, and arterial oxygen saturation. Pulse oximeters, for example, illustrate the different aspects of such monitors, and are used as an example herein.

Pulse Oximeters are commonly used to monitor the level of oxygen in the blood of a patient. This is particularly critical during an operation, or during post-operation recovery. In addition, pre-delivery monitoring of the oxygen in a fetus provides important information. A typical oximeter directs light to the skin of a patient, with either transmitted or reflected scattered light being measured by a light detector. The amount of light detected will be diminished by the amount of light absorbed by the oxygen in the patient's blood. By using appropriate wavelengths of light emitters, and their known absorption characteristics along with appropriate mathematical algorithms, the oxygen saturation of a patient can be monitored.

Because of the need to quickly react to a change in a patient's condition, it is oftentimes important for a pulse oximeter to be in a continuous monitoring mode, with alarm limits set to generate an alarm in case the patient exceeds certain parameters. It is also desirable to be able to provide a portable pulse oximeter so that it can be moved from room to room without requiring it to be plugged in to a power outlet. In such a portable pulse oximeter, power consumption is of concern, and it is desirable to minimize the power consumption. Such a portable oximeter may not only consume power in performing the measurements, but might also transmit signals to a remote host computer for monitoring. In a portable oximeter, such transmissions may be done using wireless methods.

In one existing pulse oximeter, the Nellcor N-20, a snapshot mode is provided. In this mode, the oximeter can be turned on for a short period long enough to acquire a signal and provide a pulse oximeter reading, and then automatically shuts down. This method is useful primarily for taking a reading of a healthy or stable patient, and is not useful for a patient which requires continuing monitoring due to the patient's condition. When the snapshot mode button is pushed, five pulses are qualified and an oxygen saturation and pulse rate are displayed. No more measurements are made unless the snapshot button is pressed again. If the snapshot button is not pressed for 30 seconds, the N-20 automatically turns itself off. The N-20 also has an extended mode in which it continuously takes data and calculates and displays oxygen saturation and pulse rate.

The inventors of the present invention recognized that sleep-mode techniques used in other technologies could be imported into medical diagnostic devices, such as pulse oximetry, under the appropriate conditions. In particular, a sleep mode could be entered under carefully prescribed conditions for short periods while a patient's physiological state is stable.

Sleep-mode techniques have been used in other technologies, notably for lap-top computers which run on batteries. In a typical sleep-mode, power to certain components of the computer is turned off, or they are slowed down by reducing the clock speed, to reduce power consumption. Typically, these take advantage of the fact that a computer user is not always using the computer. Thus, for instance, circuitry in the computer may detect the absence of a keystroke for a certain amount of time, and enter a sleep mode in response. Enough circuitry is left on to detect an interrupt due to a keystroke, and the rest of the circuitry is awakened on such an occurrence. Certain microprocessors have a sleep or standby mode built in, with some microprocessors being able to be shut down completely, while others accept a vastly reduced clock speed. The microprocessor will automatically save the state of its registers and take any other action necessary to be able to resume from where it left off in its program.

Certain aspects of a computer system may be required to have power supplied to them constantly. For instance, DRAM memory is required to be periodically refreshed in order to save the memory contents. Other types of memory which are non-volatile, and do not require refreshing, are available. However, non-volatile memory is typically much more expensive, and thus there is a cost/power savings trade-off.

Sleep mode techniques have also been used in other technologies. For example, U.S. Pat. No. 4,716,463 discusses the use of batteries to keep a television powered during a power failure. Sleep mode is entered automatically upon detection of a power failure. U.S. Pat. No. 5,142,684 discusses the use of a sleep mode in a portable bar code reader. U.S. Pat. No. 4,924,496 discusses the use of a sleep mode in a telephone with incoming telephone call number display capability.

A number of patents discuss various uses of a sleep mode in an implantable device such as a pacemaker. Examples include U.S. Pat. No. 4,554,920, U.S. Pat. No. 4,561,442, and U.S. Pat. No. 4,856,524. Clearly, in an implantable device which is required to run on a battery, extending battery life is important so that another operation is not necessary to remove and replace the implanted device. Pacemakers can be put into a sleep mode for a variety of conditions. In particular, these patents discuss putting the pacemaker into a sleep mode during the refractory period, which is a period between heart beats when the heart muscle is non-responsive to electrical stimuli. U.S. Pat. No. 4,404,972 discusses not only implantable pacemakers, but also implantable devices for controlling bladder function, producing muscle contractions effective to combat scoliosis, to assist in countering pain-producing nerve impulses, and to control the infusion of various solutions into the body. These devices are all therapeutic, delivering material or energy to the body at controlled times. They do not collect data for diagnostic purposes, where the condition of the patient is unknown.

SUMMARY OF THE INVENTION

The present invention provides a method and apparatus for conserving power in a medical diagnostic apparatus by using a sleep mode during a monitoring state. The invention monitors a physiological parameter of the patient and enters a sleep mode only after it has been stable for a predetermined period of time. The apparatus is periodically awakened from the sleep mode to take additional measurements and to ascertain that the stability of the physiological parameter has not changed. In one embodiment, the sleep period is chosen to be consistent with the period in which an alarm condition would need to be generated if a patient's condition started to quickly change.

3

The stable period during which sleep mode can be used may vary depending on the type of diagnostic apparatus and the characteristic being measured. Physical characteristics can include the five vital signs: heart rate, respiration rate, blood pressure, temperature and arterial oxygen saturation. Blood constituents typically include oxygen, carbon dioxide, blood glucose, hemoglobin concentration and blood analytes, such as sodium, potassium, chlorine, bicarbonate and blood urea nitrogen. Stability is defined as a condition where one or more predetermined variables change within a predetermined window of values defined by a predetermined rule set, the rule set allowing for the change to be measured in relative or absolute values, and the rule set allowing for the passage of time to constitute an integral part of the rules.

In one preferred embodiment, the apparatus is a pulse oximeter, and both the blood oxygen saturation and heart rate are monitored. These may be considered stable if the heart rate does not vary by more than 3–20% and the blood oxygen saturation does not vary by more than 2–10 saturation percentage points for a predetermined stable time period of 5–50 seconds (other preferred percentages and time periods are set forth in the description of the preferred embodiments). Upon attaining such stability, sleep mode can be entered. In a preferred embodiment, the sleep period is between 20 and 60 seconds, after which the pulse oximeter is awakened for a sufficient amount of time to make new measurements of blood oxygen saturation and heart rate. Since the patient is presumed to still be stable, the pulse oximeter does not need to use an initialization routine to acquire pulses which would typically require at least five or more pulses. Rather, data for 1–2 pulses (alternately, 1–15 pulses) is acquired and compared to the previously acquired data before re-entering the sleep mode (assuming stability is re-confirmed). If the patient has not remained stable, the sleep mode is discontinued and continuous monitoring is done until the patient is again determined to be stable.

In a preferred embodiment, a majority of the pulse oximeter electronic circuitry is turned off, excepting in particular a memory storing the data acquired while the patient was stable. Elements which are turned off in a sleep mode include the CPU, the light emitting diodes and driver circuitry, as well as the analog-to-digital converter connected to the detector. Preferably, the circuitry is turned off for a period of 20 seconds, and then awakened to acquire data associated with two pulse maximums. Alternately, the pulse oximeter could be put in a sleep mode in between pulses, such as preferably during the diastolic decay portion of a heart pulse (after the maximum and before the minimum).

An additional requirement for entering sleep mode in one embodiment is that the patient be stable at a "high" saturation value. High is preferably defined as being a predetermined amount higher than the alarm limit of the oximeter for low saturation or heart rate.

For a fuller understanding of the nature and advantages of the invention, reference should be made to the ensuing detailed description taken in conjunction with the accompanying drawings.

4

DETAILED DESCRIPTION OF THE PREFERRED EMBODIMENTS

Figure 1:
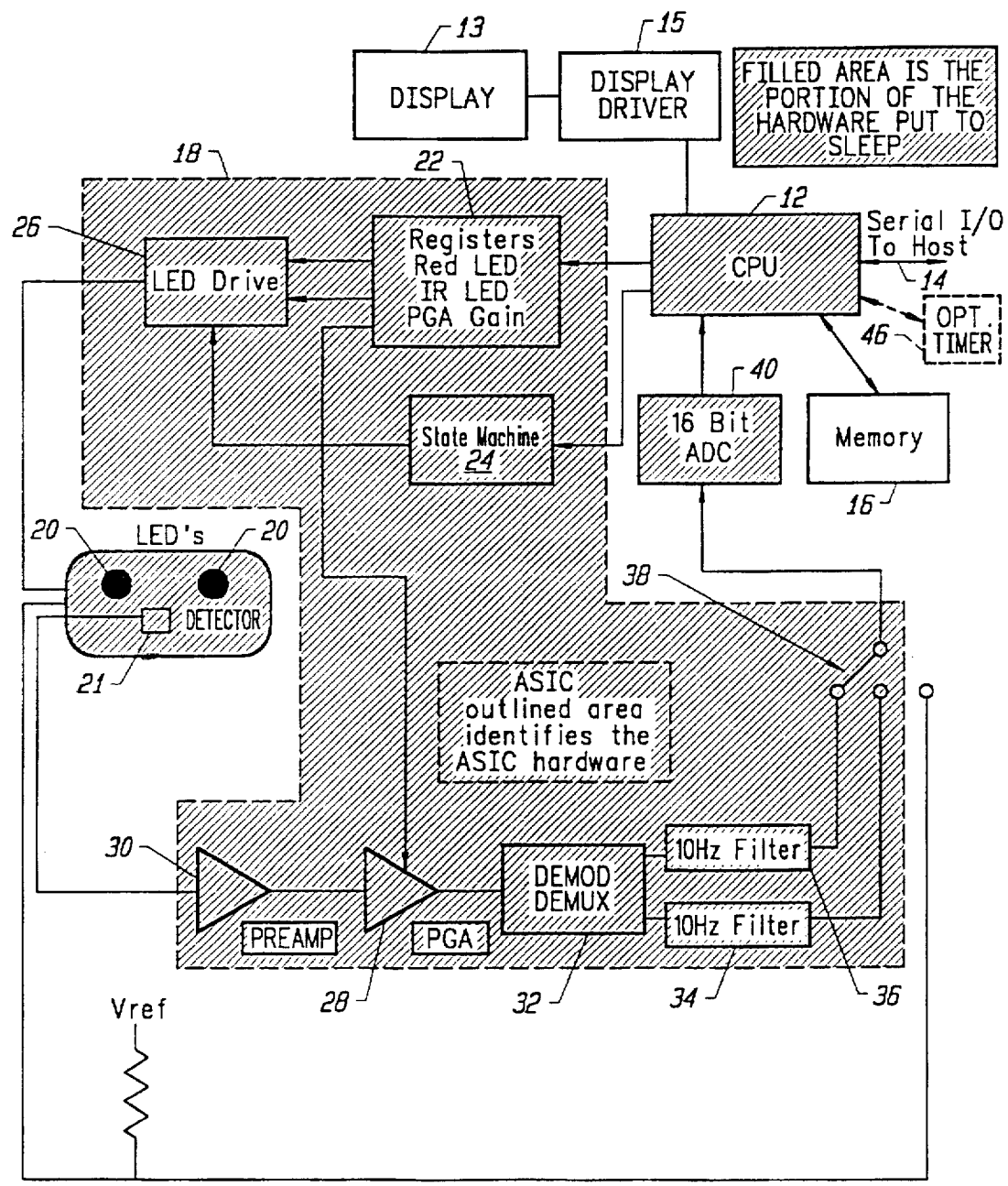
FIG. 1 is a block diagram of a pulse oximeter with sleep mode according to the present invention.

The present invention applies to a diagnostic device which enters a sleep mode while a patient is stable. By way of example, a pulse oximeter is described, although the invention could apply to any diagnostic device. FIG. 1 is a block diagram of one embodiment of a pulse oximeter according to the present invention, illustrating an example of the type of components which could be put into a sleep mode to conserve power. The pulse oximeter includes a CPU 12 which may be connected by a serial I/O port 14 to a remote host computer. Port 14 can either be a hardwired connection or a wireless connection. CPU 12 is connected to its own memory 14. The CPU is also connected to electronic circuitry in the form of an Application Specific Integrated Circuit (ASIC) 18 which includes the drive and detection circuitry for a pair of Light Emitting Diodes (LEDs) 20 which provide light to the patient's skin.

As shown, ASIC 18 includes a number of registers 22 and a state machine 24. State machine 24 offloads some of the routine functions from CPU 12, such as the alternate switching and controlling of power levels for the drive circuitry 26 connected to the two LEDs 20. In addition, the state machine 24 adjusts the gain of a programmable gain circuit 28 which adjusts the signal detected in a light detector 21 associated with LEDs 20 and provided through a preamplifier 30. Typically, this gain is adjusted to take maximum advantage of the range of the analog-to-digital converter to provide more sensitivity for smaller signals, and more range for larger signals.

Completing the circuitry is a demodulator/demultiplexer 32 which provides the detected signal through two different filters 34 and 36 and a switch 38 to an analog-to-digital converter (ADC) 40.

During a sleep mode, all the elements shown in FIG. 1 except for memory 16 are put into a sleep mode. "Sleep mode" may mean the removal of power, or the use of a lower power state, such as a slower clock frequency for CPU 12.

The oximeter also has a display 13 and a display driver 15. This will typically include a numeric display of the heart rate and the oxygen saturation. In addition, there may be a bar graph which rises and falls with the heart rate, or a waveform display. In a sleep mode, some or all of the display may be put into a sleep mode. Preferably, the numerical displays continue to receive power and are active in a sleep mode, while any bar/blip display and waveform display is disabled. The CPU can thus provide the display driver 15 with the latest data before the CPU goes to sleep, with display driver 15 staying awake and maintaining the last data throughout the sleep mode period. Power is saved by limiting the amount of display illuminated. Alternate methods are possible, such as dimming the numerical display during sleep mode or having a slow, blinking display to save additional power. Preferably, the numeric display is maintained constantly to make the sleep mode somewhat transparent to the user.

When put into the sleep mode, the pulse oximeter can be awakened by a signal from the remote host on I/O line 14 (which can be a wire or wireless telemetry connection). Alternately, a stand-alone pulse oximeter may have its own optional timer 46 which is set by the CPU before going into sleep mode. The timer will then generate an interrupt to the CPU upon expiration of the sleep mode time to awaken the CPU.

Figure 2:
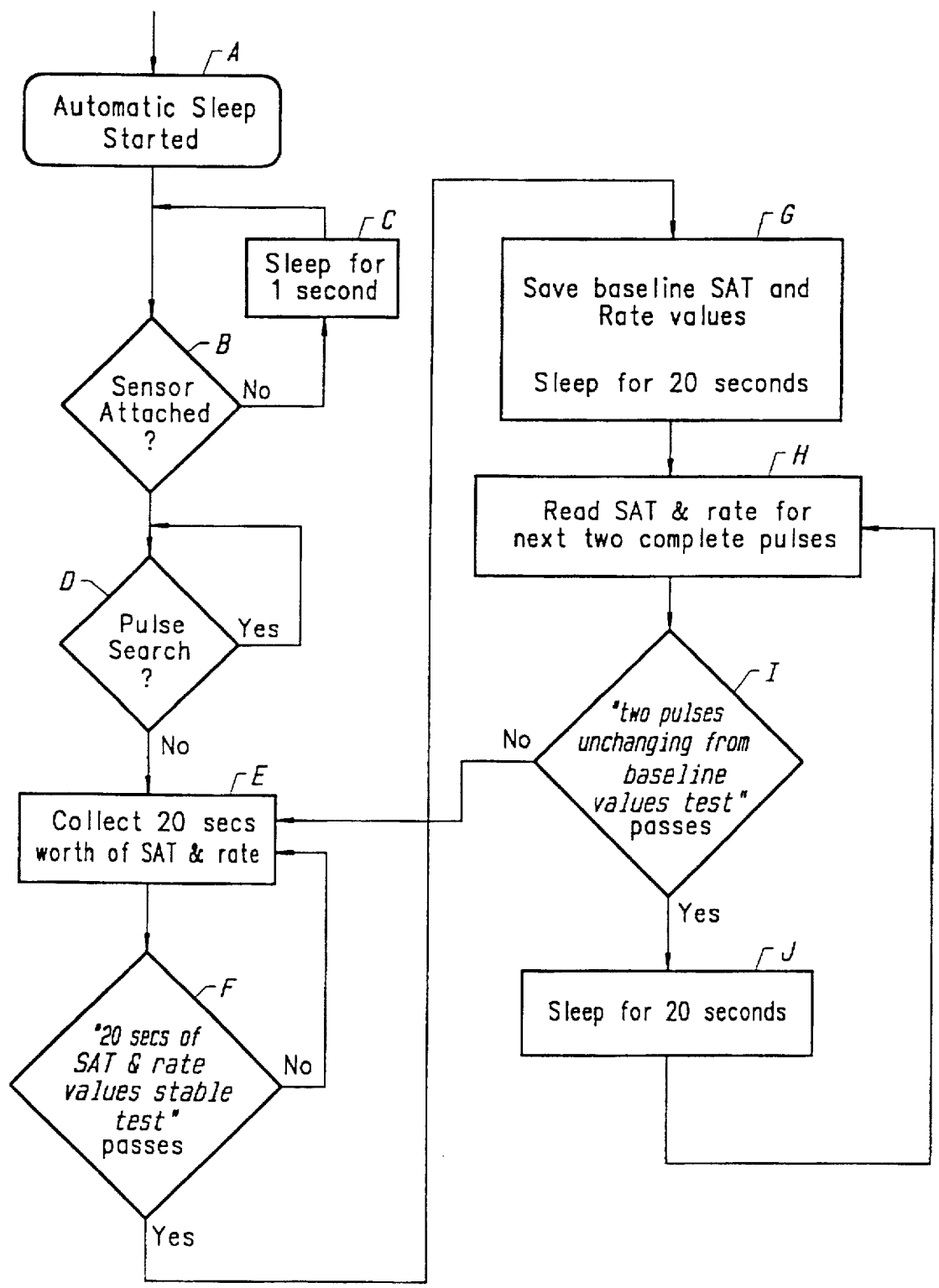
FIG. 2 is a flow chart of the automatic sleep mode according to the present invention.

FIG. 2 is a flow chart illustrating the automatic sleep mode control flow of the present invention. It should be noted that in addition to the automatic sleep mode, a manual mode can be provided wherein the host can provide a signal to instruct the pulse oximeter to go into a sleep mode, and remain there until awakened by the host. In such a mode, the host would provide the necessary timing.

As shown in FIG. 2, in a first step A, automatic sleep mode is started. After the pulse oximeter is turned on, it first determines whether a sensor is attached to the oximeter (step B). If no sensor is attached, the pulse oximeter is put into a sleep mode for one second, and then is reawakened to test again whether a sensor is attached. Since typically only around 200 microseconds are required to determine if a sensor is attached, this provides a significant power savings even though the sleep mode is for only one second at a time. In this mode, the pulse oximeter is thus asleep for around 80% of the time.

Once a sensor has been attached, the oximeter searches for a detectable pulse pattern to lock onto or "acquire." In this type of pulse oximeter, the cardiac pulse is first detected so that the oximeter readings can be made at the same position in subsequent pulses. This is done because the volume of blood changes depending upon the portion of the pulse, thus changing the oximeter reading due to more light being absorbed with the presence of more oxygenated blood in one portion of the pulse compared to another. Once a pulse has been acquired, there is no longer any pulse search, and the oximeter then proceeds to collect blood oxygen saturation data and heart rate data (step E). The data is continuously tested to see whether it passes the stability test compared to previous samples during a 20 second period (step F). If at any time during the 20 second period the stability test fails, the test is reset.

A 20-second stability period is chosen for the preferred embodiment, although other periods of time may be chosen, preferably 5, 7, 10, 15, 20, 25, 30, 40 or 50 seconds, and most preferably at least 15-20 seconds. The stability criteria in the preferred embodiment is that the heart rate not vary more than 5%, although other variation limits may be used, preferably no more than 20%, more preferably 15%, more preferably 10%, optionally more than 5% or 3%. The clinical empirical tests known to the inventors show that a ±5 beats per minute (bpm) variation of heart rate can be expected from a normal patient during the course of oximetry monitoring. In addition to the heart rate, in the preferred embodiment, the oxygen saturation value may not vary more than two saturation points out of a maximum scale of 100 in order to be stable. Alternately, this stability limit is preferably chosen to be less than 10, 8, 6, 5, 4, 3 or 2 saturation percentage points. The inventors have determined by empirical test that a ±2% variation of oxygen saturation (SAT) can be expected from a normal patient during the course of oximetry monitoring. Alternately, the saturation variation can be a percentage of the optimum saturation for the patient or last saturation value. This would be significant, for example, where a normal adult with a saturation in the high nineties is compared to a fetus with a saturation typically in the seventies or lower. An absolute limit of 1% of a 100-point range produces different percentage values of a normal saturation in a healthy adult versus a fetus, and accordingly, different limits may optionally be imposed.

If the patient is determined to be stable, sleep mode is entered (step G). Sleep mode is entered by first saving the baseline oxygen saturation value (SAT) and heart rate value in memory 16. The pulse oximeter then goes to sleep for a period of 20 seconds in the preferred embodiment. In the study of apnea, the normally accepted times when a patient is to be checked are 15, 20 or 30 seconds. Preferably, the sleep period is no more than 60, 50, 40, 35, 30, 25, 20 or 15 seconds. Optionally, the same period of time used to determine stability (preferably 20 seconds) is also used for the sleep period between checks of the patient (also 20 seconds).

Upon awakening from the sleep mode, the saturation and heart rate value are read for the next two complete pulses (step H). These are compared to the baseline values stored in memory from the stability period (step I). If the values collected during the two pulses are within the baseline value limits, indicating the patient is still stable, sleep mode is reentered for another 20 seconds (step J). Otherwise, the continuous monitoring operation is reinstated, and the sleep mode cannot be entered again until at least 20 seconds of stable data have again been collected.

The two pulses read when the pulse oximeter awakes from the sleep mode are preferably not used to adjust the baseline value, though optionally they could be so used. Keeping the baseline fixed prevents the baseline from slowly changing without having to be stable for a 20-second period. The number of pulses read upon awakening need not be two, but is preferably 1, 2, 3, 5, 8, 10 or 15 pulses. In one embodiment, if the oximeter has been in the sleep mode for a series of 20 second periods, more time may be spent in the awake state to re-establish the average, stable values, while still realizing a significant power savings. This can be done without a significant overall effect on power consumption, since significant power savings have already been achieved. For example, in one embodiment, if the oximeter has been in a continuous series of sleep modes for more than 1-2 minutes, the oximeter could remain awake for 5 pulses, rather than 2, to establish and calculate a new average heart rate and oxygen saturation. The awake periods chosen can alternatively be time based, as opposed to pulse based as previously described, in which case preferable awake time periods could include any one of 1, 2, 3, 5, 8, 10, and 15 seconds, with 2, 3, and 5 seconds being preferred embodiments. Some pulse oximeters use saturation calculation algorithms which are not event based (e.g., pulse based) but rather use data for saturation calculation without regard to where the data is located relative to the cardiac pulse.

The limits for heart rate and blood oxygen saturation to determine stability could be varied depending upon a variety of factors. For example, the type of patient could be used to vary the standard, especially for blood oxygen saturation between a fetus and an adult. Alternately, depending upon the method used to acquire the data, a different limit could be used depending upon the amount of averaging used in the evaluation method. The host computer dynamically adjusts these limits in one embodiment.

In one embodiment, the pulse oximeter is not allowed to go into sleep mode unless the patient is stable at a "high" saturation value. "High" could be defined as a predetermined number, or in relation to a low alarm limit, if one is used. For example, high could be greater than 90 or 95 saturation points for an adult, and greater than 50, 55, 60, or 65 for a fetus. Alternately, high could be 5, 10 or 15 saturation points above a low alarm limit, which could be, i.e., 70, 75, 80, 85, 90 or 95 for an adult, or 10, 15, 20, 25, 30, 35, 40, 45, 50, 55, 60 or 65 for a fetus. Similarly, sleep mode could be restricted if the heart rate is outside a predetermined range, or if any other monitored physiological parameter is outside a predetermined range. The host can adjust the high saturation and heart rate test settings, depending on the type of patient being monitored, the condition of the patient, whether the patient is awake or asleep, or for any other reason.

In addition, other aspects of the pulse oximeter operation may be modified during a sleep mode. In particular, a pulse oximeter includes alarm limits, such as an alarm which may be generated if no pulse is detected for a predetermined period of time (such as 10 seconds). It may be desirable to impose a shorter limit upon awakening from a sleep mode since the condition may have been continuing undetected some time prior to the awakening. In one embodiment, the "no pulse" alarm will be generated if no pulse is detected for 5 seconds after awakening, as opposed to the normal 10 seconds.

A description of different states an oximeter could be in, including noise, motion and alarm states, is set forth in U.S. Pat. No. 5,368,026 (the "'026 patent"), the disclosure of which is hereby incorporated herein by reference. Optionally, an oximeter may be required to be in a normal state, as set forth in the '026 patent, for a period of 20 seconds before sleep mode is entered. In another embodiment, sleep mode is allowed in the presence of motion, but upon awakening from the sleep mode, it must be additionally determined that motion is absent long enough to confirm stable readings before the oximeter is put back to sleep.

A manual or remotely controlled sleep mode is also provided, where the host computer controls when the oximeter is put to sleep and when it is awakened. The host computer may receive inputs from other monitors, such as an EKG or a CO2 monitor, and could use heart rate information derived from these, for instance, to determine if a patient is stable. The CO2 monitor could also provide an indication of the amount of oxygen the patient is receiving. The host could also be operated in response to a human operator viewing the patient through a remote TV monitor, or the human operator could simply decide the patient doesn't need to be monitored while awake and/or during the daytime, or only periodically during the night, or for other reasons. In one embodiment, the host can periodically determine stability separately from the pulse oximeter monitor with data from other sources, eliminating the need for the pulse oximeter to establish or reconfirm stability itself.

Preferably, the pulse oximeter responds differently to a command from the host computer to go into sleep mode, depending on the mode the pulse oximeter is in. If the pulse oximeter does not have a sensor attached, it will wake itself from the sleep mode every second to check for a sensor attached, and will continue sending no sensor attached messages to the host. If the oximeter is in the middle of performing a noise measurement when it receives the sleep command, it will preferably complete that measurement and defer entering the sleep mode for up to 2 seconds. If the oximeter is in the process of adjusting LED brightness or amplifier gains, sleep mode may be deferred for up to one second.

Depending on the state the oximeter was in when it received a sleep mode command from the host, it will respond differently when it is awakened by the host. If was doing a pulse search, it will continue the pulse search upon being awakened. If it was reporting valid SAT and heart rate information, it will wait for the next good pulse. If a good pulse is detected in 10 seconds, it will continue with normal pulse oximetry measurements. If no good pulse is detected in 10 seconds, a pulse time out occurs, with an alarm being generated, unless a probationary state has been entered for motion as set forth in the '026 Patent.

Upon reawakening the pulse oximeter from a manual sleep mode, it can go into an automatic sleep mode operation. Preferably, the oximeter must always cycle through a normal monitoring mode (20 seconds) before entering an automatic sleep mode after a manual sleep mode.

Figure 3:
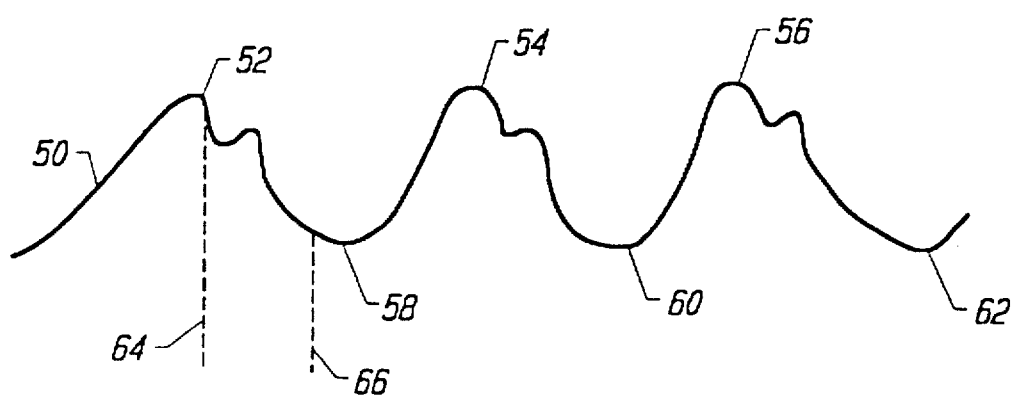
FIG. 3 is a diagram of a heart pulse illustrating periods during which sleep mode can be entered.

FIG. 3 is a diagram of the optical pulse which may be received by the pulse oximeter. This waveform 50 includes a series of peaks 52, 54, and 56, along with intervening minimums 58, 60, and 62. Typically, the pulse oximeter measurements are made on the rising edge of the pulse oximeter waveform, such as between minimum 58 and maximum 54 or between minimum 60 and maximum 56. Accordingly, in an alternate embodiment, the pulse oximeter could be put to sleep during a diastolic decline after a maximum and before the next minimum. For example, the sleep mode could be entered in the period between dotted lines 64 and 66 for each pulse. Preferably, a margin of at least 5% of the length of the trailing edge of the pulse is used after the maximum and before the expected minimum to allow for variations in the occurrence of the minimum and to avoid false peak triggering on the maximum. Since the trailing edge of the pulse is typically 75% of the total pulse time, this sleep mode can produce a significant power savings.

To achieve additional power savings, the two techniques can be combined. That is, during normal operation, when it is being determined if a patient is stable, the pulse oximeter could still sleep between points 64 and 66 for each pulse. Since only the rising edge of the pulse wave form is needed, this would not degrade the determination of blood oxygenation and heart rate so long as the pulse does not vary so much from pulse to pulse that the sleep window ends up extending beyond the falling edge. This can be avoided by providing sufficient margin for the next anticipated minimum to reawaken from sleep mode. Upon entering a normal sleep mode, the operation of the pulse oximeter to acquire data during two pulses could also be put to sleep during the falling edges of those two pulses to further conserve power.

As will be understood by those with skill in the art, the present invention may be embodied in other specific forms without departing from the spirit or essential characteristics thereof. For example, only some of the electronic circuitry put to sleep might be awakened for a new measurement. Alternately, the circuitry might be awakened only to do a measurement, and not to determine stability, or vice-versa. For instance, stability might be re-verified only after several sleep periods. In another example, a sleep mode could be used for a heart rate monitor, a blood pressure monitor, a respiration monitor, a temperature monitor, or any other type of diagnostic monitor. A respiration monitor, for example, could sleep for a period of time similar to that for a pulse oximeter. Sleep mode could be restricted, for example, based on the carbon dioxide content of the patient's exhaled breath. A temperature monitor, for example, could have a much longer sleep mode, since temperature changes occur much slower than oxygen deprivation, which could occur very quickly. A blood constituent monitor could alternately monitor carbon dioxide; blood glucose; hemoglobin concentration; and blood analytes, such as sodium, potassium, chlorine, bicarbonate, and blood urea nitrogen. Alternately, the circuitry could be distributed, with wireless connections, and only portions subject to the sleep mode. Accordingly, the foregoing description is illustrative of the invention, but reference should be made to the following claims which set forth the scope of the invention.

What is claimed is:

1. A method for conserving power in a pulse oximeter apparatus, said apparatus including electronic circuitry, the method comprising the steps of:

(a) measuring a blood oxygen saturation of a patient using said apparatus;

(b) monitoring said blood oxygen saturation of said patient;

(c) determining when said blood oxygen saturation has been stable for a predetermined stable time period and providing a stability indication signal;

(d) initiating a sleep mode for at least a portion of said electronic circuitry, in response to said stability indication signal, for a first, sleep portion of each of a plurality of sleep mode time periods;

(e) exiting said sleep mode for at least some of said portion of electronic circuitry for a second, awake portion of each of said plurality of sleep mode time periods;

(f) determining whether said blood oxygen saturation remains stable during at least periodic ones of said sleep mode time periods;

(g) repeating steps (a)–(f) if said blood oxygen saturation is determined to not have remained stable during said awake portion; and (h) repeating steps (c)–(f) if said blood oxygen saturation is determined to have remained stable during said awake portion.

2. The method of claim 1 wherein said blood oxygen saturation is stable if it has not varied by more than a predetermined limit which is no greater than 5 saturation points out of a scale of 100 saturation points.

3. The method of claim 1 wherein said predetermined stable time period is at least 15 seconds.

4. The method of claim 1 further comprising the step of monitoring a heart rate of said patient, and producing said stability indication signal only if said heart rate is also stable, said heart rate being stable if it does not vary more than a predetermined limit which is less than ten percent from a previous value in at least a 15 second period.

5. The method of claim 4 wherein said pulse oximeter includes a display and further comprising the step of deactivating all diagnostic displays except a numerical indication of oxygen saturation and heart rate on said display during said sleep mode.

6. The method of claim 1 wherein said portion of said electronic circuitry in said sleep mode includes a light emitter driver, a CPU and an analog-to-digital converter, and does not include a memory.

7. The method of claim 1 further comprising the step of controlling the initiation and exiting of said sleep mode with a remote host computer.

8. The method of claim 1 wherein said sleep mode time period comprises a plurality of cardiac pulse periods.

9. The method of claim 1 wherein said sleep portion of said sleep mode time period is no more than 30 seconds.

10. The method of claim 1 wherein step (b) is performed over a plurality of cardiac pulse periods, each of the cardiac pulse periods comprises a diastolic period, and the method further comprises the step of entering the sleep mode during the diastolic period of each of the cardiac pulse periods.

11. The method of claim 1 further comprising the steps of:
determining whether a sensor is attached to said pulse oximeter;
entering said sleep mode for a short sleep time shorter than said first, sleep period if no sensor is attached; and
testing whether a sensor is attached during an awake portion of said sleep mode time period.

12. The method of claim 1 wherein said apparatus includes a display, and further comprising the steps of:
deactivating at least a portion of said display during said sleep mode.

13. The method of claim 1 further comprising the steps of:
determining whether said blood oxygen saturation has been greater than a predetermined value during said stable time period; and
providing said stability indication signal only if said blood oxygen saturation has been greater than said predetermined value during said stable time period.

14. The method of claim 1 further comprising the steps of:
providing an alarm signal in response to a pre-specified physiological condition of a patient or a condition of said apparatus continuing for an alarm time-out period; and
shortening said alarm time-out period upon exiting said sleep mode.

15. A method for conserving power in a pulse oximeter, said pulse oximeter having light emitters and electronic circuitry including a CPU, an analog-to-digital converter and a memory, the method comprising the steps of:

(a) monitoring the blood oxygen saturation of a patient using said pulse oximeter;

(b) monitoring the heart rate of said patient;

(c) determining when said blood oxygen saturation and said heart rate have been stable for a stable time period of at least 15 seconds and providing a stability indication signal, said blood oxygen saturation being stable if it has not varied by more than a predetermined blood oxygen saturation limit which is less than 5 saturation points out of a scale of 100 saturation points, said heart rate being stable if it does not vary more than a predetermined heart rate limit which is less than ten percent from a previous value in at least a 15 second period;

(d) initiating a sleep mode for said light emitters and at least said CPU and analog-to-digital converter, in response to said stability indication signal, for a first, sleep portion of each of a plurality of sleep mode time periods, said sleep portion being no more than 40 seconds;

(e) exiting said sleep mode for said light emitters and said electronic circuitry for a second, awake portion of each of said plurality of sleep mode time periods;

(f) determining whether said blood oxygen saturation and heart rate remain stable during said awake portion of said sleep mode time period;

(g) repeating steps (a)–(f) if either of said blood oxygen saturation and heart rate is determined to not have remained stable during said awake portion; and (h) providing the stability indication signal and repeating steps (d)–(f) if both said blood oxygen saturation and heart rate are determined to have remained stable during said awake portion.

16. A pulse oximeter with a power saving feature, comprising:

a CPU;

a memory coupled to said CPU;

light emitter drive circuitry coupled to said CPU;

light detector receiving circuitry;

an analog-to-digital converter coupled to said light emitter receiving circuitry and to said CPU;

means, coupled to said CPU, for monitoring the blood oxygen saturation of a patient using said pulse oximeter;

means, coupled to said CPU, for monitoring at least one additional physiological parameter of said patient;

means, coupled to said CPU, for determining when said blood oxygen saturation has been stable for a predetermined stable time period and providing a stability indicating signal;

means, coupled to said CPU, for initiating a sleep mode for said light emitter drive circuitry and at least said CPU and said analog-to-digital converter, in response to said stability indication signal, for a first, sleep portion of each of a plurality of sleep mode time periods;

means, coupled to said CPU, for exiting said sleep mode for said light emitter drive circuitry, said CPU and said analog-to-digital converter for a second, awake portion of each of said plurality of sleep mode time periods;

means, coupled to said CPU, for determining whether said blood oxygen saturation remains stable during said awake portion of said sleep mode time period; and means, coupled to said CPU, for reinitiating said sleep mode for said light emitter drive circuitry and at least said CPU and said analog-to-digital converter, if said physiological parameter is determined to have remained stable during said awake portion.

17. The pulse oximeter of claim 15 wherein said blood oxygen saturation is stable if it has not varied by more than a predetermined limit which is no greater than 5 saturation points out of a scale of 100 saturation points.

18. The pulse oximeter of claim 15 wherein said means for monitoring also monitors a heart rate of said patient and provides said stability indication signal only if said heart rate is also stable, said heart rate being stable if it does not vary more than a predetermined limit which is less than ten percent from a previous value in at least a 15 second period.

19. The pulse oximeter of claim 16 wherein said predetermined stable time period is at least 15 seconds.

20. The pulse oximeter of claim 16 further comprising:

a remote host computer; and means for controlling the initiation and exiting of said sleep mode with said remote host computer.

21. The pulse oximeter of claim 16 wherein said sleep mode time period comprises a plurality of cardiac pulse periods.

22. The pulse oximeter of claim 21 wherein said sleep portion of said sleep mode time period is no more than 30 seconds.

23. The pulse oximeter of claim 16 wherein said means for monitoring monitors said physiological parameter over a plurality of cardiac pulse periods, each cardiac pulse period including a diastolic period, and the pulse oximeter further comprises means for entering the sleep mode during the diastolic period of each of the cardiac pulse periods.

24. The pulse oximeter of claim 16 further comprising:

means for determining whether a sensor is attached to said pulse oximeter;

means for entering said sleep mode for a short sleep time shorter than said first, sleep period if no sensor is attached; and means for testing whether a sensor is attached during an awake portion of said sleep mode time period.

25. The pulse oximeter of claim 16 further comprising:

a display;

means for deactivating at least a portion of said display during said sleep mode.

26. The pulse oximeter of claim 23 further comprising:

means for measuring said blood oxygen saturation and a heart rate of said patient; and means for deactivating all diagnostic displays except a numerical indication of oxygen saturation and heart rate on said display during said sleep mode.

27. The pulse oximeter of claim 16 further comprising:

means for determining whether said blood oxygen saturation has been greater than a predetermined value during said stable time period; and means for providing said stable indication signal only if said blood oxygen saturation has been greater than said predetermined value during said stable time period.

28. The pulse oximeter of claim 16 further comprising:

means for providing an alarm signal in response to a pre-specified condition of an oximeter signal continuing for an alarm time-out period; and means for shortening said alarm time-out period upon exiting said sleep mode.

29. The pulse oximeter of claim 16 further comprising a separate monitor connected to said CPU, for monitoring said additional physiological parameter.

* * * * *